(12) United States Patent
Chowaniec et al.

(10) Patent No.: US 12,029,422 B2
(45) Date of Patent: *Jul. 9, 2024

(54) SURGICAL STAPLER ADAPTER WITH FLEXIBLE CABLE ASSEMBLY, FLEXIBLE FINGERS, AND CONTACT CLIPS

(71) Applicant: Covidien LP, Mansfield, MA (US)

(72) Inventors: David Chowaniec, Rocky Hill, CT (US); Ethan Collins, Naugatuck, CT (US); Pawel Abramek, Berlin, CT (US); Ryan Williams, New Hartford, CT (US); Matthew Chowaniec, Madison, CT (US)

(73) Assignee: Covidien LP, Mansfield, MA (US)

( * ) Notice: Subject to any disclaimer, the term of this patent is extended or adjusted under 35 U.S.C. 154(b) by 115 days.

This patent is subject to a terminal disclaimer.

(21) Appl. No.: 17/851,594

(22) Filed: Jun. 28, 2022

(65) Prior Publication Data

US 2022/0323071 A1 Oct. 13, 2022

Related U.S. Application Data

(63) Continuation of application No. 16/670,611, filed on Oct. 31, 2019, now Pat. No. 11,369,372.
(Continued)

(51) Int. Cl.
*A61B 17/072* (2006.01)
*H01R 12/77* (2011.01)
(Continued)

(52) U.S. Cl.
CPC ...... *A61B 17/072* (2013.01); *A61B 17/07207* (2013.01); *H01R 12/771* (2013.01);
(Continued)

(58) Field of Classification Search
CPC ............... A61B 17/068; A61B 17/072; A61B 17/07207; A61B 17/115;
(Continued)

(56) References Cited

U.S. PATENT DOCUMENTS

| 37,165 A | 12/1862 | Gary |
| 3,209,754 A | 10/1965 | Brown |

(Continued)

FOREIGN PATENT DOCUMENTS

| CN | 101683284 A | 3/2010 |
| CN | 102648864 A | 8/2012 |

(Continued)

OTHER PUBLICATIONS

Office Action issued in corresponding Chinese Application No. 201911141302.X mailed Jul. 8, 2023, together with English language translation (14 pages).
(Continued)

*Primary Examiner* — Scott A Smith
(74) *Attorney, Agent, or Firm* — Carter, DeLuca & Farrell LLP

(57) ABSTRACT

A surgical device includes a handle assembly including a controller and a first electrical connector. The surgical device also includes an adapter assembly having: a tubular housing having a proximal end portion configured to couple to the handle assembly, and a distal end portion; a second electrical connector disposed at the proximal end portion and configured to couple to the first electrical connector; an electrical contact assembly disposed at the distal end portion; and a wire harness disposed within the tubular housing and interconnecting the second electrical connector and the electrical contact assembly. The surgical device also includes a surgical end effector configured to couple to the distal end portion of the adapter assembly, the surgical end
(Continued)

effector includes an electrical contact configured to couple to the electrical contact assembly.

20 Claims, 13 Drawing Sheets

Related U.S. Application Data

(60) Provisional application No. 62/772,281, filed on Nov. 28, 2018.

(51) Int. Cl.
*H01R 13/625* (2006.01)
*A61B 17/00* (2006.01)
*A61B 17/068* (2006.01)
*A61B 17/115* (2006.01)

(52) U.S. Cl.
CPC .. *H01R 13/625* (2013.01); *A61B 2017/00017* (2013.01); *A61B 2017/00473* (2013.01); *A61B 2017/00477* (2013.01); *A61B 17/068* (2013.01); *A61B 2017/07214* (2013.01); *A61B 2017/07257* (2013.01); *A61B 2017/07271* (2013.01); *A61B 2017/07285* (2013.01); *A61B 17/115* (2013.01); *H01R 2201/12* (2013.01)

(58) Field of Classification Search
CPC .. A61B 2017/00017; A61B 2017/0046; A61B 2017/00473; A61B 2017/00477; A61B 2017/07214; A61B 2017/07228
USPC .............. 227/19, 175.1, 175.2, 176.1, 180.1; 606/1, 139, 219
See application file for complete search history.

(56) References Cited

U.S. PATENT DOCUMENTS

| | | |
|---|---|---|
| 3,273,562 A | 9/1966 | Brown |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |

(56) References Cited

U.S. PATENT DOCUMENTS

| | | |
|---|---|---|
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt et al. |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,305,970 B1 | 10/2001 | Nagai et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,375,492 B1 | 4/2002 | Hio |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |

(56) References Cited

U.S. PATENT DOCUMENTS

| | | |
|---|---|---|
| 6,515,273 B2 | 2/2003 | Ai-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,823,760 B2 | 11/2010 | Zemlok et al. |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 8,006,885 B2 | 8/2011 | Marczyk |
| 8,006,887 B2 | 8/2011 | Marczyk |
| 8,011,551 B2 | 9/2011 | Marczyk et al. |
| 8,020,742 B2 | 9/2011 | Marczyk |
| 8,025,199 B2 | 9/2011 | Whitman et al. |
| 8,038,044 B2 | 10/2011 | Viola |
| 8,052,024 B2 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,240,536 B2 | 8/2012 | Marczyk |
| 8,240,537 B2 | 8/2012 | Marczyk |
| 8,267,924 B2 | 9/2012 | Zemlok et al. |
| 8,328,823 B2 | 12/2012 | Aranyi et al. |
| 8,348,125 B2 | 1/2013 | Viola et al. |
| D865,174 S * | 10/2019 | Auld ............................ D24/145 |
| 11,213,293 B2* | 1/2022 | Worthington .... A61B 17/00234 |
| 11,369,372 B2* | 6/2022 | Chowaniec .......... A61B 17/072 |
| 2002/0103489 A1 | 8/2002 | Ku |
| 2002/0111641 A1 | 8/2002 | Peterson et al. |
| 2002/0165541 A1 | 11/2002 | Whitman |
| 2003/0090201 A1 | 5/2003 | Peng |
| 2003/0114851 A1 | 6/2003 | Truckai et al. |
| 2003/0120306 A1 | 6/2003 | Burbank et al. |
| 2004/0232201 A1 | 11/2004 | Wenchell et al. |

(56) References Cited

U.S. PATENT DOCUMENTS

| | | |
|---|---|---|
| 2005/0006429 A1 | 1/2005 | Wales et al. |
| 2005/0010235 A1 | 1/2005 | VanDusseldorp |
| 2005/0131390 A1 | 6/2005 | Heinrich et al. |
| 2005/0139636 A1 | 6/2005 | Schwemberger et al. |
| 2005/0177176 A1 | 8/2005 | Gerbi et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0219563 A1 | 9/2007 | Voegele |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0135600 A1 | 6/2008 | Hiranuma et al. |
| 2008/0169329 A1 | 7/2008 | Shelton et al. |
| 2008/0185419 A1 | 8/2008 | Smith et al. |
| 2008/0197167 A1 | 8/2008 | Viola et al. |
| 2008/0255413 A1 | 10/2008 | Zemlok et al. |
| 2008/0255607 A1 | 10/2008 | Zemlok |
| 2009/0018624 A1 | 1/2009 | Levinson et al. |
| 2009/0090201 A1 | 4/2009 | Viola |
| 2009/0090763 A1 | 4/2009 | Zemlok et al. |
| 2010/0200636 A1 | 8/2010 | Zemlok et al. |
| 2010/0312257 A1 | 12/2010 | Aranyi |
| 2010/0320254 A1 | 12/2010 | Zemlok et al. |
| 2011/0034910 A1 | 2/2011 | Ross et al. |
| 2011/0062211 A1 | 3/2011 | Ross et al. |
| 2011/0168757 A1 | 7/2011 | Viola et al. |
| 2011/0172681 A1 | 7/2011 | Aranyi et al. |
| 2011/0190738 A1 | 8/2011 | Zemlok et al. |
| 2011/0218522 A1 | 9/2011 | Whitman |
| 2011/0301579 A1 | 12/2011 | Marczyk et al. |
| 2011/0303735 A1 | 12/2011 | Marczyk |
| 2012/0055972 A1 | 3/2012 | Marczyk |
| 2012/0074197 A1 | 3/2012 | Marczyk |
| 2012/0175400 A1 | 7/2012 | Viola et al. |
| 2012/0193393 A1 | 8/2012 | Viola et al. |
| 2012/0198288 A1 | 8/2012 | Njo et al. |
| 2012/0220989 A1 | 8/2012 | Zemlok et al. |
| 2012/0223121 A1 | 9/2012 | Viola et al. |
| 2012/0241494 A1 | 9/2012 | Marczyk |
| 2012/0277790 A1 | 11/2012 | Zemlok et al. |
| 2012/0298718 A1 | 11/2012 | Marczyk |
| 2012/0298720 A1 | 11/2012 | Marczyk |
| 2015/0280384 A1 | 10/2015 | Leimbach et al. |
| 2015/0374371 A1 | 12/2015 | Richard et al. |
| 2016/0095585 A1 | 4/2016 | Zergiebel et al. |
| 2016/0106424 A1 | 4/2016 | Yates |
| 2016/0310134 A1 | 10/2016 | Contini et al. |
| 2017/0224347 A1 | 8/2017 | Collins et al. |
| 2018/0168592 A1* | 6/2018 | Overmyer ........ A61B 17/07207 |
| 2018/0233850 A1 | 8/2018 | Penna et al. |
| 2018/0303481 A1* | 10/2018 | Shelton, IV ..... A61B 17/07207 |
| 2018/0317921 A1 | 11/2018 | Cabrera |
| 2019/0000471 A1* | 1/2019 | Shelton, IV .......... A61B 17/29 |
| 2019/0015097 A1* | 1/2019 | Williams ............. A61B 17/068 |

FOREIGN PATENT DOCUMENTS

| | | |
|---|---|---|
| CN | 107595341 A | 1/2018 |
| EP | 0537570 A2 | 4/1993 |
| EP | 0647431 A2 | 4/1995 |
| EP | 0738501 A1 | 10/1996 |
| EP | 0770354 A1 | 5/1997 |
| EP | 1070487 A2 | 1/2001 |
| EP | 1201196 A1 | 5/2002 |
| EP | 1658817 A1 | 5/2006 |
| EP | 1813203 A2 | 8/2007 |
| EP | 3205289 A1 | 8/2017 |
| EP | 3398527 A1 | 11/2018 |
| EP | 3412225 A1 | 12/2018 |
| EP | 3476331 A1 | 5/2019 |
| EP | 3560436 A1 | 10/2019 |
| EP | 3738501 A1 | 11/2020 |
| FR | 2849589 A1 | 7/2004 |
| WO | 9414129 A1 | 6/1994 |
| WO | 9729694 A1 | 8/1997 |
| WO | 9740760 A1 | 11/1997 |
| WO | 9837825 A1 | 9/1998 |
| WO | 9952489 A1 | 10/1999 |
| WO | 0234140 A2 | 5/2002 |
| WO | 03026511 A1 | 4/2003 |
| WO | 03030743 A2 | 4/2003 |
| WO | 2004032760 A2 | 4/2004 |
| WO | 2007030753 A2 | 3/2007 |
| WO | 2007114868 A2 | 10/2007 |
| WO | 2007118179 A2 | 10/2007 |
| WO | 2007014355 A3 | 4/2009 |
| WO | 2009143092 A1 | 11/2009 |
| WO | 2016171947 A1 | 10/2016 |

OTHER PUBLICATIONS

Detemple, P., "Microtechnology in Modern Health Care", Med Device Technol. 9(9):18-25 (1998).

Abridged Data Sheet, "DeepCover Secure Authenticator with 1-Wire SHA-256 and 512-Bit User EEPROM", Maxim Integrated Products, Inc. pp. 1-4; 42; Dec. 2012.

Data Sheet "DS28E15-1-Sire SHA-256 Secure Authenticator with 512-Bit User EEPROM" ; IC-On-Line, Electronic Component Manufacturers, pp. 1-2; Aug. 2013.

Extended European Search Report dated Apr. 20, 2020 issued in corresponding EP Appln. No. 19211852.9.

European Examination Report issued in corresponding application EP 19 211 852.9 dated Jun. 29, 2023 (8 pages).

* cited by examiner

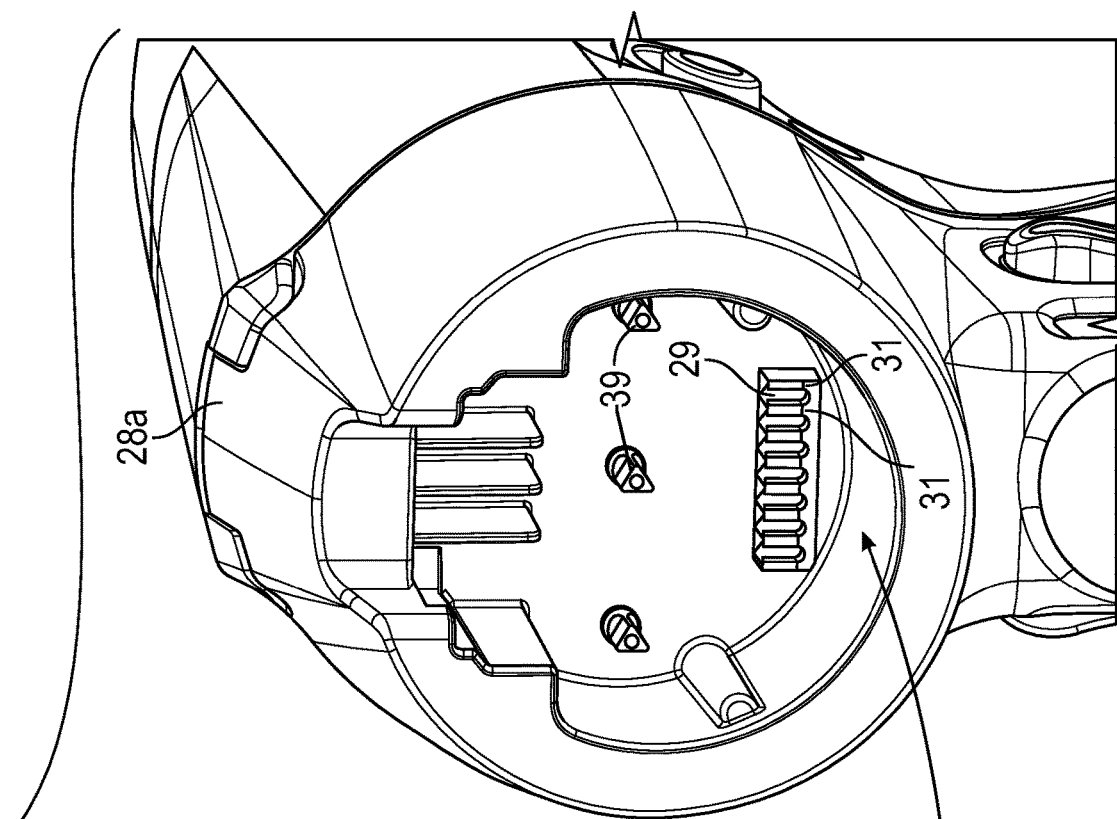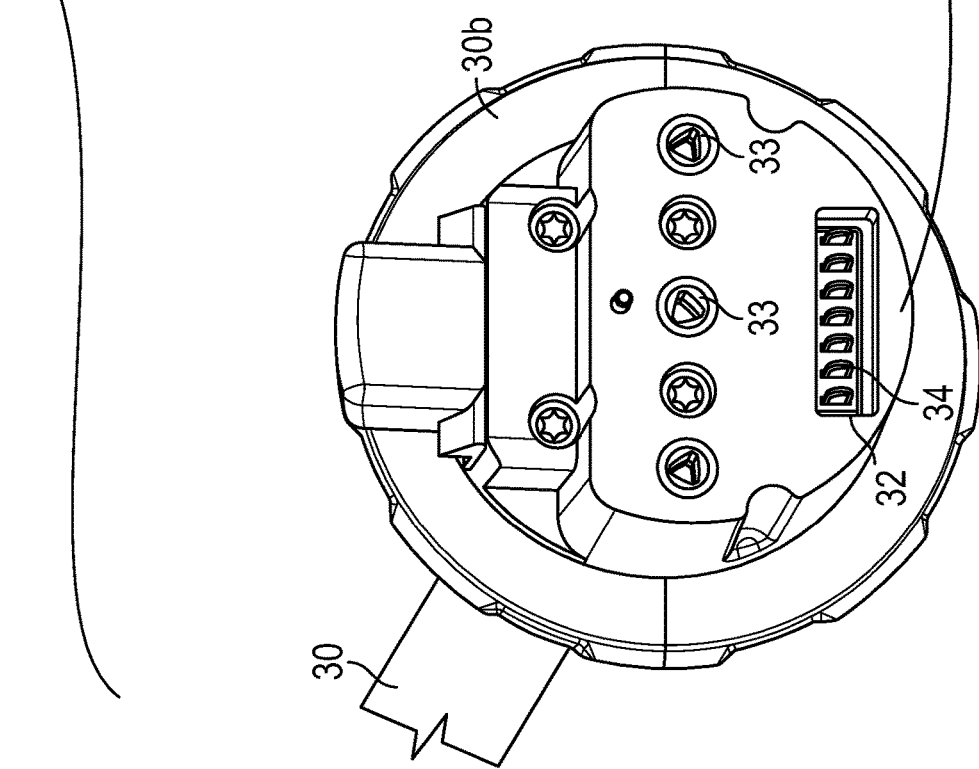
FIG. 2

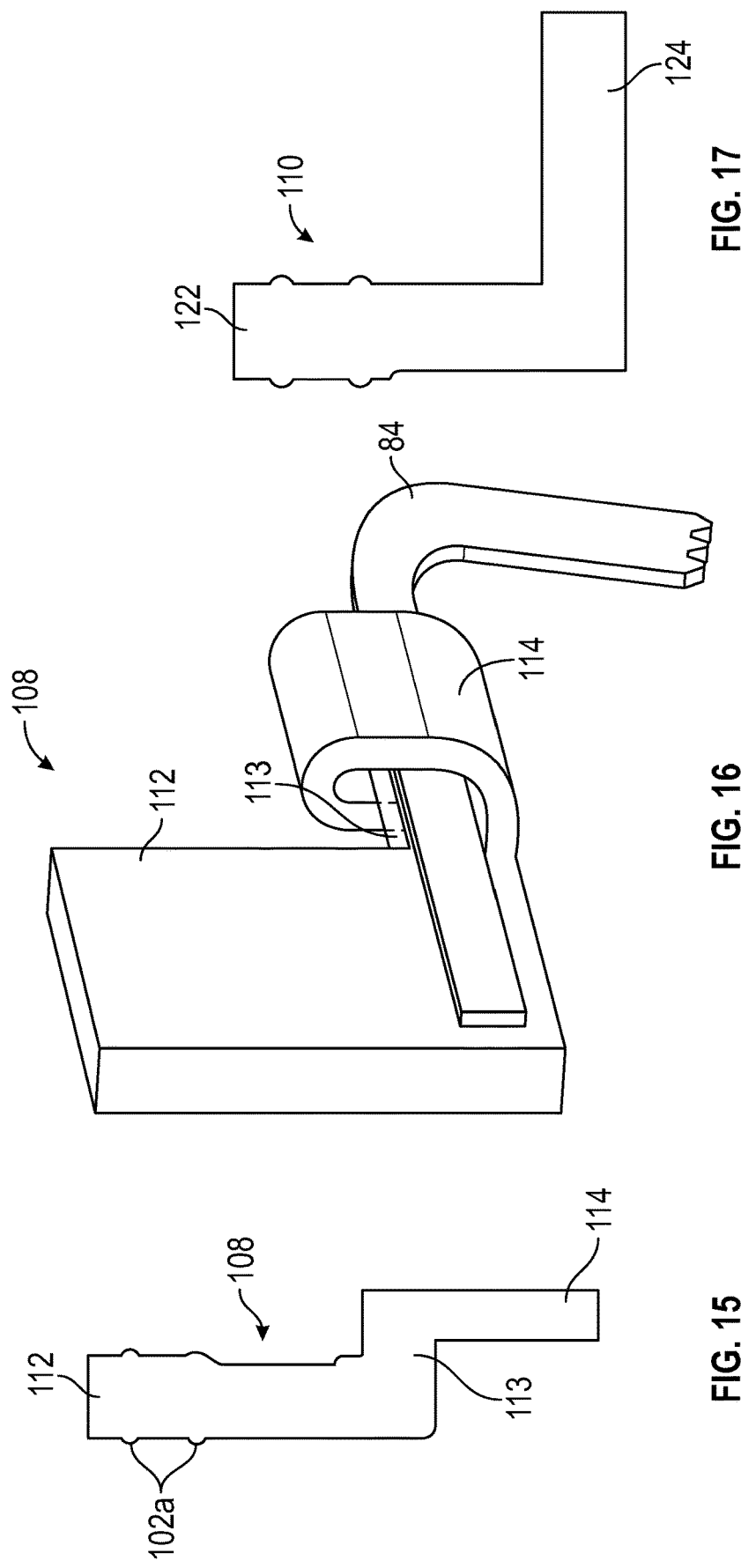

SURGICAL STAPLER ADAPTER WITH FLEXIBLE CABLE ASSEMBLY, FLEXIBLE FINGERS, AND CONTACT CLIPS

CROSS-REFERENCE TO RELATED APPLICATIONS

This application is a continuation of U.S. patent application Ser. No. 16/670,611, filed on Oct. 31, 2019, now U.S. Pat. No. 11,369,372, which claims the benefit of and priority to U.S. Provisional Patent Application Ser. No. 62/772,281, filed Nov. 28, 2018. The entire disclosure of each of these applications are incorporated by reference herein.

BACKGROUND

1. Technical Field

The present disclosure relates to surgical devices. More specifically, the present disclosure relates to adapter assemblies for use with surgical stapler devices having electrical contacts that clip onto flexible fingers of a flexible cable.

2. Background of Related Art

Surgical fastener devices for applying fasteners or staples to tissue are well known. These fastener devices include single use devices which are preloaded with one or more staples and are disposable after a single use. Multiple use devices are also available and are preloaded with a plurality of staples. Multiple use devices may include a handle assembly that is electromechanically, e.g., powered, or manually actuated. These devices may be used with single use loading units (SULU) or multiple use loading units (MULU). The loading units include a body and an end effector, and are attached to the handle assembly, either directly or via an adapter assembly couplable to the handle assembly.

A number of surgical device manufacturers have developed product lines with proprietary powered drive systems for operating and/or manipulating the surgical device. The powered handle assembly and the loading unit may be electrically interconnected. Accordingly, the adapter assemblies include electrical components, such as cables, switches, circuit boards, and the like. Thus, there is a need for electrical connectors suitable for use with the adapter assemblies that can withstand mechanical stresses encountered during use.

SUMMARY

According to one embodiment of the present disclosure, a surgical device is disclosed. The surgical device includes a handle assembly including a controller and a first electrical connector. The surgical device also includes an adapter assembly having: a tubular housing having a proximal end portion configured to couple to the handle assembly, and a distal end portion; a second electrical connector disposed at the proximal end portion and configured to couple to the first electrical connector; an electrical contact assembly disposed at the distal end portion; and a wire harness disposed within the tubular housing and interconnecting the second electrical connector and the electrical contact assembly. The surgical device also includes a surgical end effector configured to couple to the distal end portion of the adapter assembly, the surgical end effector includes an electrical contact configured to couple to the electrical contact assembly.

According to another embodiment of the present disclosure, a surgical device adapter assembly is disclosed. The surgical device adapter assembly includes: a tubular housing having a proximal end portion configured to couple to a handle assembly, and a distal end portion configured to couple to a surgical end effector; an electrical connector disposed at the proximal end portion; an electrical contact assembly disposed at the distal end portion; and a wire harness disposed within the tubular housing and interconnecting the electrical connector and the electrical contact assembly.

According to one aspect of any of the above embodiments, the wiring harness is a flexible cable. The adapter assembly may further include a switch actuated in response to the surgical end effector being coupled to the adapter assembly. The flexible cable may be coupled to the switch and include a flexible finger coupled to the electrical contact assembly.

According to one aspect of any of the above embodiments, the adapter assembly may include a rotatable lock member. The electrical contact assembly may include a housing having a cantilevered tongue configured to attach the electrical contact assembly to the rotatable lock member.

According to a further aspect of any of the above embodiments, the electrical contact assembly may also include a contact clip secured in a depression formed on the housing. The flexible finger may be electrically coupled to the contact clip, which may include a contact portion and an attachment portion that is configured to engage the electrical contact. The attachment portion may be folded over to secure the flexible finger to the contact clip. The flexible finger may include an exposed portion of a conductive layer that is soldered to the contact clip.

BRIEF DESCRIPTION OF THE DRAWINGS

Embodiments of the present disclosure are described herein with reference to the accompanying drawings, wherein:

FIG. 2 is a perspective view illustrating a connection of the adapter assembly and the handle assembly of FIG. 1 according to an embodiment of the present disclosure;

FIG. 15 is a top view of a contact clip according to an embodiment of the present disclosure;

FIG. 16 is a perspective view of the contact clip of FIG. 15;

FIG. 17 is a top view of a contact clip according to another embodiment of the present disclosure;

DETAILED DESCRIPTION OF EMBODIMENTS

Figure 1:
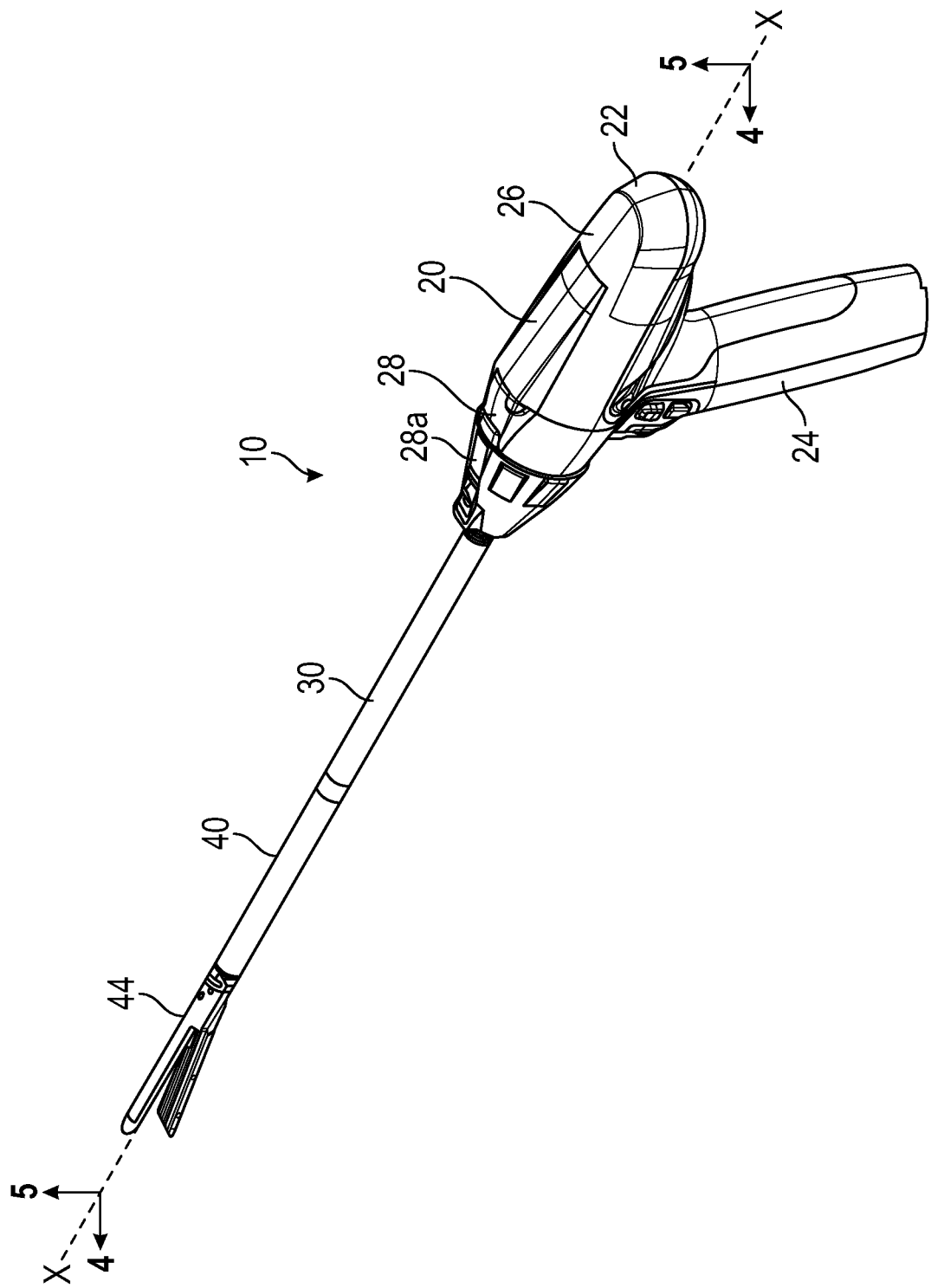
FIG. 1 is a perspective view of a handheld surgical device, an adapter assembly, an end effector according to an embodiment of the present disclosure.

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

The present disclosure provides an adapter assembly including a flexible cable running longitudinally within the adapter assembly. The adapter assembly interconnects a handle assembly and a loading unit. The cable transfers electrical signals from a rotating ring, which engages a loading unit, to the handle assembly. The flexible cable avoids using stranded wires to transfer signals from the rotating ring to the flexible cable by using the wires with fingers incorporated directly into a distal end of the flexible cable. The flexible fingers are soldered to contact clips of the electrical contact assemblies which are attached to the rotating ring. The contact clips conduct signals from the loading unit. The contact clips have features which clip onto the flexible fingers to relieve stress from the solder joints themselves. In particular, coupling flexible fingers of the flexible cable to the electrical contact assemblies, which are in turn coupled to the rotatable lock member imparts physical strain onto the electrical connection between the flexible fingers and the electrical contact assemblies. The present disclosure, which relies on soldering and securing the flexible fingers directly to the respective electrical contact clips, mitigates the mechanical stress imparted on the flexible fingers and the electrical contact clips due to rotation of the rotatable lock member, which prevents the flexible fingers from detaching from the electrical contact assemblies.

Use of a single flexible cable also reduces the number of parts used in the adapter assembly by obviating the need for additional wires. Using wire connectors also requires cutting wires to length and stripping to a predetermined length. Soldering the wires and creating service loops to relieve stress from the solder joints is also a labor-intensive process. The flexible fingers eliminate the need for the cutting/stripping process and providing slack loops. Manufacturing the flexible fingers to the proper length is more repeatable and easier to control than cutting and stripping the wires. The assembly of the distal electronics system is also more repeatable with the flexible fingers. The flexible cable may be printed in a flat state and formed into the desired configuration during the assembly process. Dimensions of the flexible cable may also easily be adjusted and reprinted for optimization.

With reference to FIG. 1, a powered surgical device 10 includes a handle assembly 20, which is configured for selective connection with an adapter assembly 30, which in turn, is configured for selective connection with a loading unit 40 having an end effector 44. Although generally referred to as being a powered surgical device, it is contemplated that the surgical device 10 may be manually actuated and may include various configurations.

The handle assembly 20 includes a handle housing 22 having a lower housing portion 24, an intermediate housing portion 26 extending from and/or supported on a portion of the lower housing portion 24, and an upper housing portion 28 extending from and/or supported on a portion of the intermediate housing portion 26. As shown in FIG. 2, a distal portion of the upper housing portion 28 defines a nose or connecting portion 28a that is configured to accept a proximal end portion 30b of the adapter assembly 30.

Figure 3:
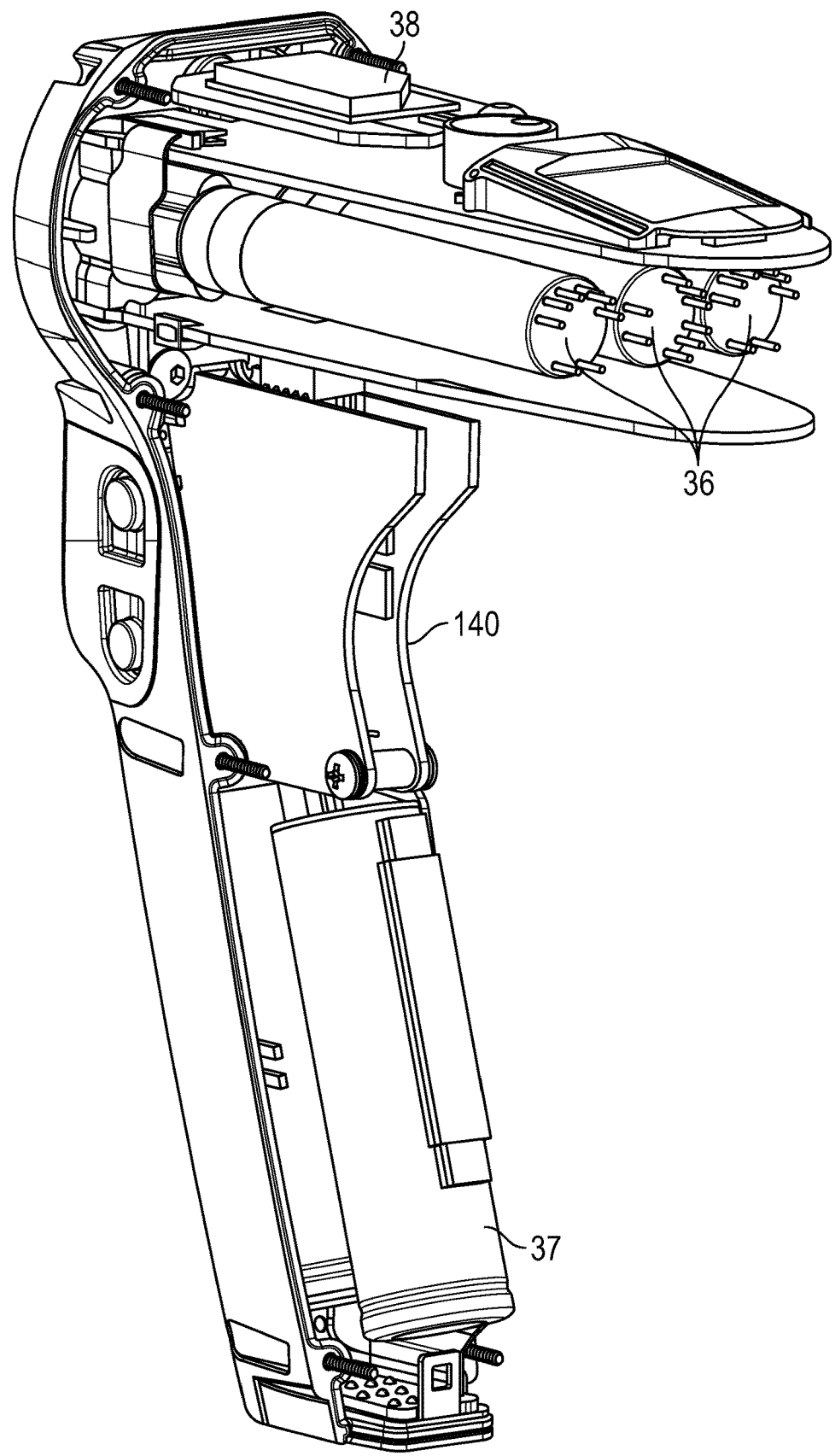
FIG. 3 is perspective view of internal components of the handle assembly according to an embodiment of the present disclosure.

With reference to FIG. 2, the connecting portion 28a of the upper housing portion 28 includes an electrical receptacle 29 having a plurality of electrical contacts 31, which are in electrical communication with electronic (e.g., main controller 38) and electrical components (e.g., power source 37) of the handle assembly 20 (FIG. 3). The adapter assembly 30 includes a counterpart electrical connector 32 that is configured to engage the electrical receptacle 29. The electrical connector 32 also includes a plurality of electrical contacts 34 that engage and electrically connect to their counterpart electrical contacts 31.

With reference to FIG. 3, the handle assembly 20 includes one or more motors 36 which are coupled to a power source 37. The handle assembly 20 also includes a main controller 38 for operating the motors 36 and other electronic components of the handle assembly 20, the adapter assembly 30, and the loading unit 40. The motors 36 are coupled to corresponding drive shafts 39 (FIG. 2), which are configured to engage sockets 33 on the proximal end portion 30b, such that rotation of the drive shafts 39 is imparted on the sockets 33.

Figure 4:
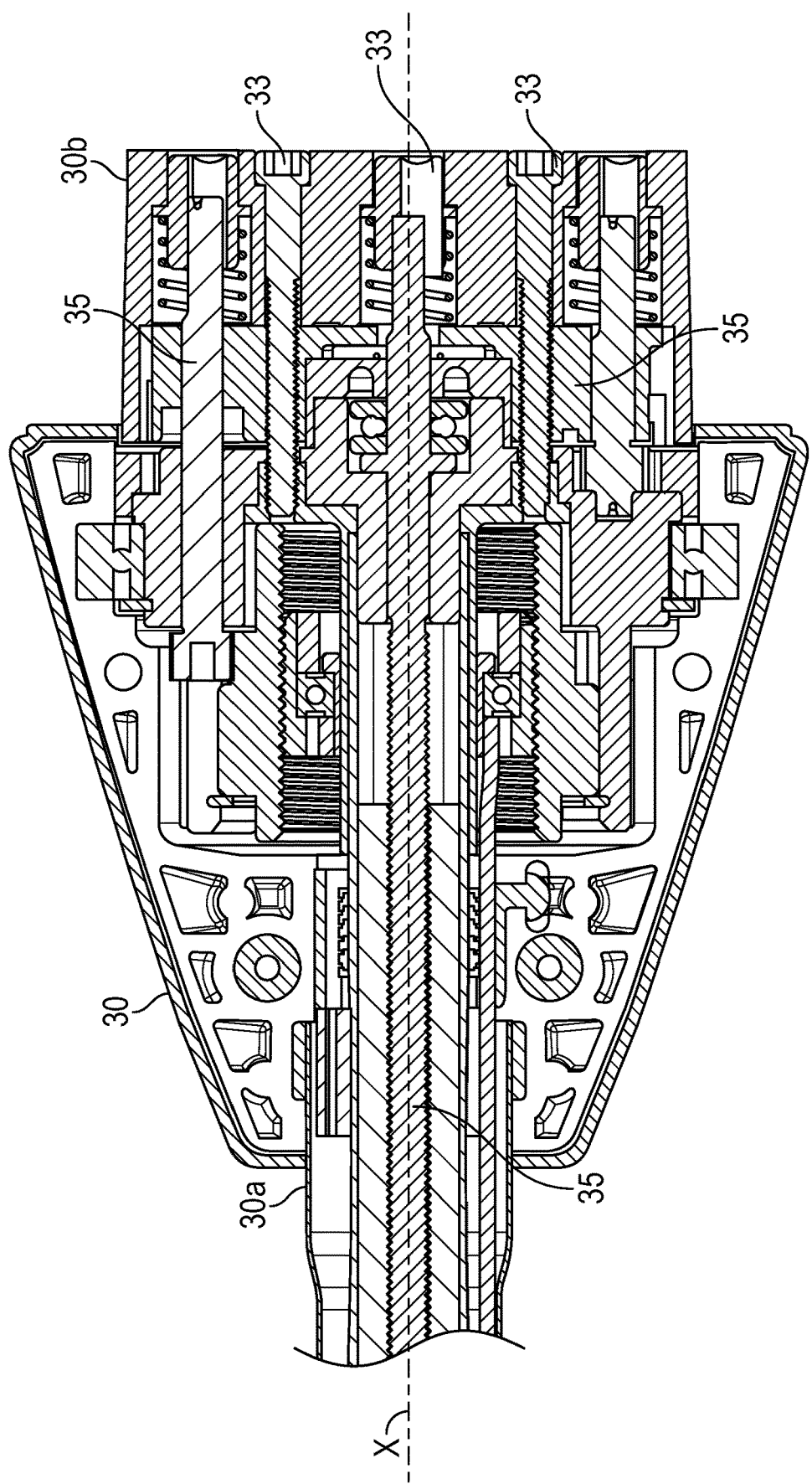
FIG. 4 is cross-sectional view of the adapter assembly taken along a section plane "4-4" of FIG. 1 according to an embodiment of the present disclosure.
Figure 5:
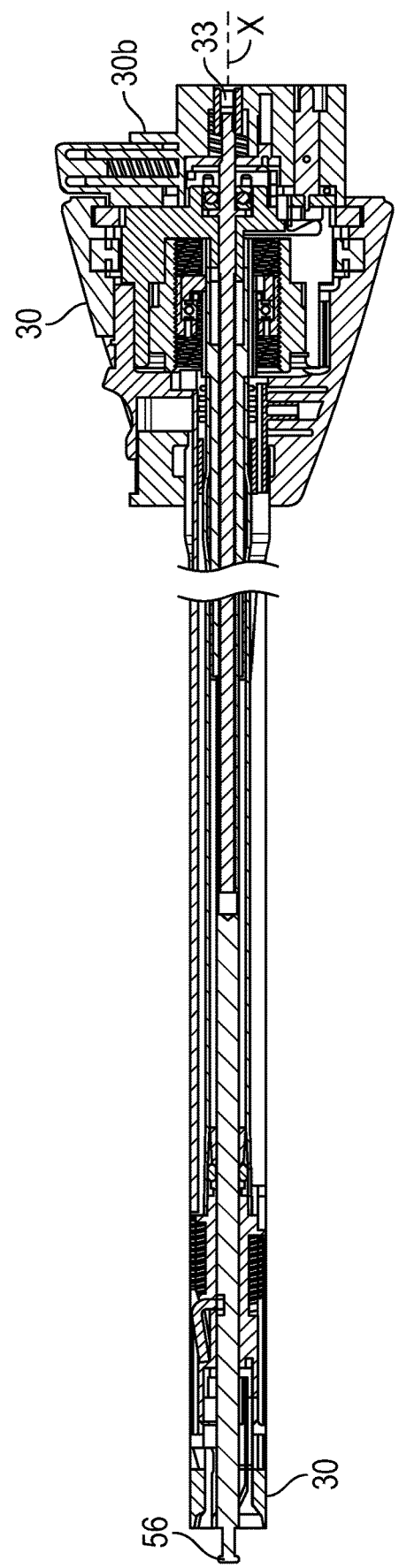
FIG. 5 is cross-sectional view of the adapter assembly taken along a section plane "5-5" of FIG. 1 according to an embodiment of the present disclosure.

With reference to FIGS. 4 and 5, the adapter assembly 30 includes a tubular housing 30a that extends between a proximal end portion 30b that is configured for operable connection to the connecting portion 28a of the handle assembly 20 and an opposite, distal end portion 30c that is configured for operable connection to the loading unit 40. The adapter assembly 30 includes actuation assemblies 35 each of which is coupled to one of the sockets 33. The actuation assemblies 35 are configured to transfer rotational motion of the sockets 33 into linear motion and/or rotational motion, such that the adapter assembly 30 is configured to convert a rotational motion provided by the handle assembly 20 into axial translation for rotating the adapter assembly 30 about a longitudinal axis X-X, articulate the loading unit 40, clamp tissue, eject fasteners, and cut fastened tissue.

Figure 6:
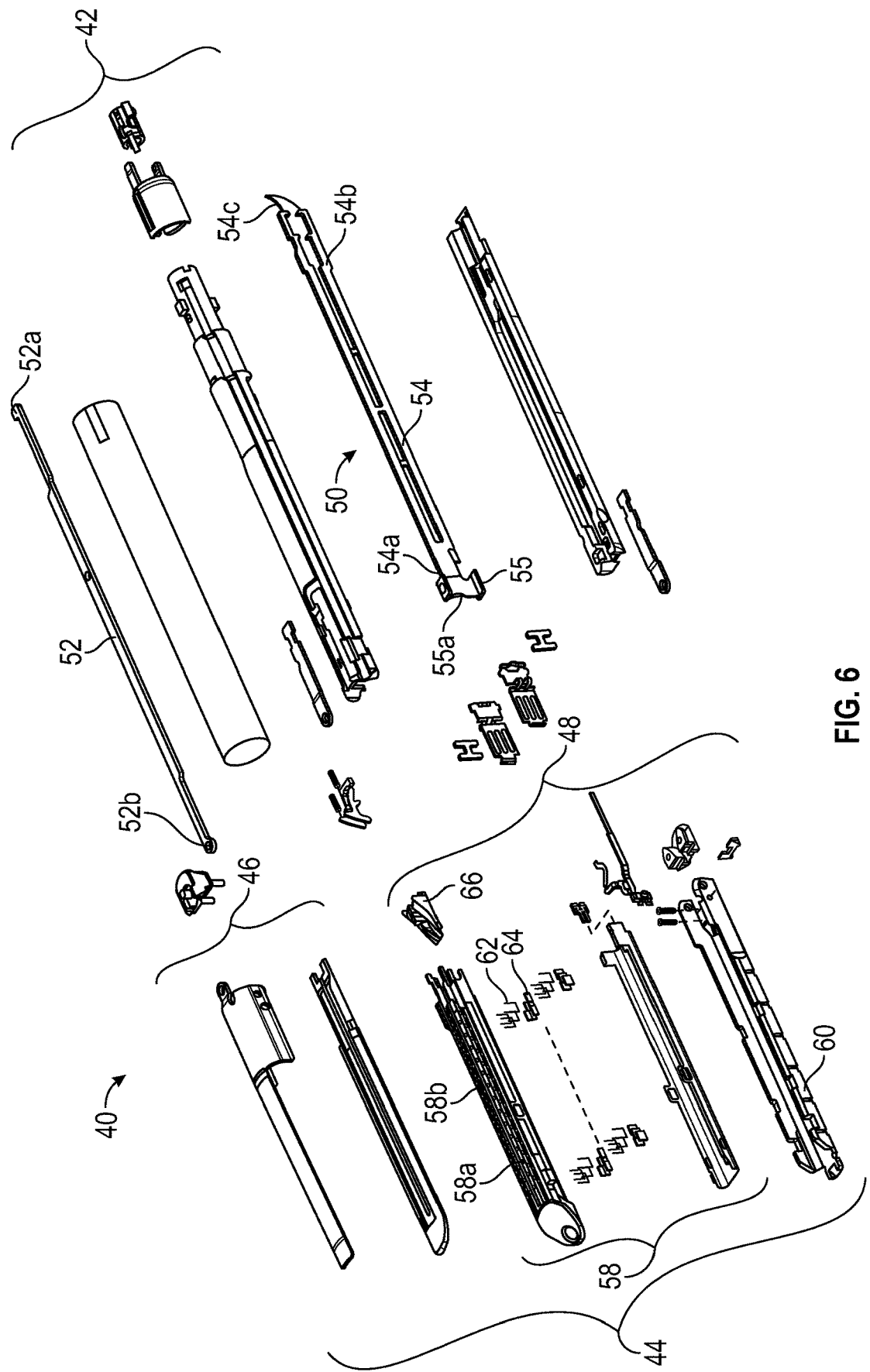
FIG. 6 is a perspective view, with parts separated, of the surgical loading unit of FIG. 1.

With reference to FIGS. 1 and 6, an embodiment of the loading unit 40 is shown. The loading unit 40 includes a proximal body portion 42 and a surgical end effector 44. Proximal body portion 42 is releasably attached to the distal end portion 30c of adapter assembly 30, and end effector 44 is pivotally attached to a distal end of proximal body portion 42. End effector 44 includes an anvil assembly 46 and a cartridge assembly 48. Cartridge assembly 48 is pivotal in relation to anvil assembly 46 and is movable between an open or unclamped position and a closed or clamped position. Proximal body portion 42 includes a drive assembly 50 and an articulation link 52.

Drive assembly 50 includes a flexible drive beam 54 having a distal end portion 54a and a proximal engagement section 54b. The distal end portion 54a includes an I-beam 55 having a knife 55a. The I-beam 55 is configured to travel through the anvil assembly 46 and the cartridge assembly 48, thereby pushing the anvil assembly 46 toward the cartridge assembly 48 to clamp tissue. The proximal engagement section 54b includes diametrically opposed inwardly extending fingers 54c that engage a drive member 56 (FIG. 5) to fixedly secure drive member 56 to the proximal end of drive beam 54. Drive member 56 is actuated by one of the actuation assemblies 35 of adapter assembly 30.

Cartridge assembly 48 of end effector 44 includes a staple cartridge 58 removably supported in a carrier 60. Staple cartridge 58 defines a central longitudinal slot 58a, and a plurality of linear rows of staple retention slots 58b positioned on each side of the central longitudinal slot 58a. Each of the staple retention slots 58b receives a single staple 62 and a portion of a staple pusher 64. During operation of the surgical device 10, drive assembly 50 abuts an actuation sled 66 and pushes actuation sled 66 through the staple cartridge 58. As the actuation sled 66 moves through staple cartridge 58, cam wedges of the actuation sled 66 sequentially engage staple pushers 64 to move staple pushers 64 vertically within staple retention slots 58b and sequentially eject a single staple 62 therefrom for formation against an anvil plate 46a of anvil assembly 46.

Proximal body portion 42 of surgical loading unit 40 includes an articulation link 52 having a hooked proximal end portion 52a which extends from a proximal end of surgical loading unit 40 which engages an opposing articulation link (not shown) coupled to another one of the actuation assemblies 35 of the adapter assembly 30. Articulation link 52 has a distal end portion 52b pivotably secured to end effector 44.

Figure 7:
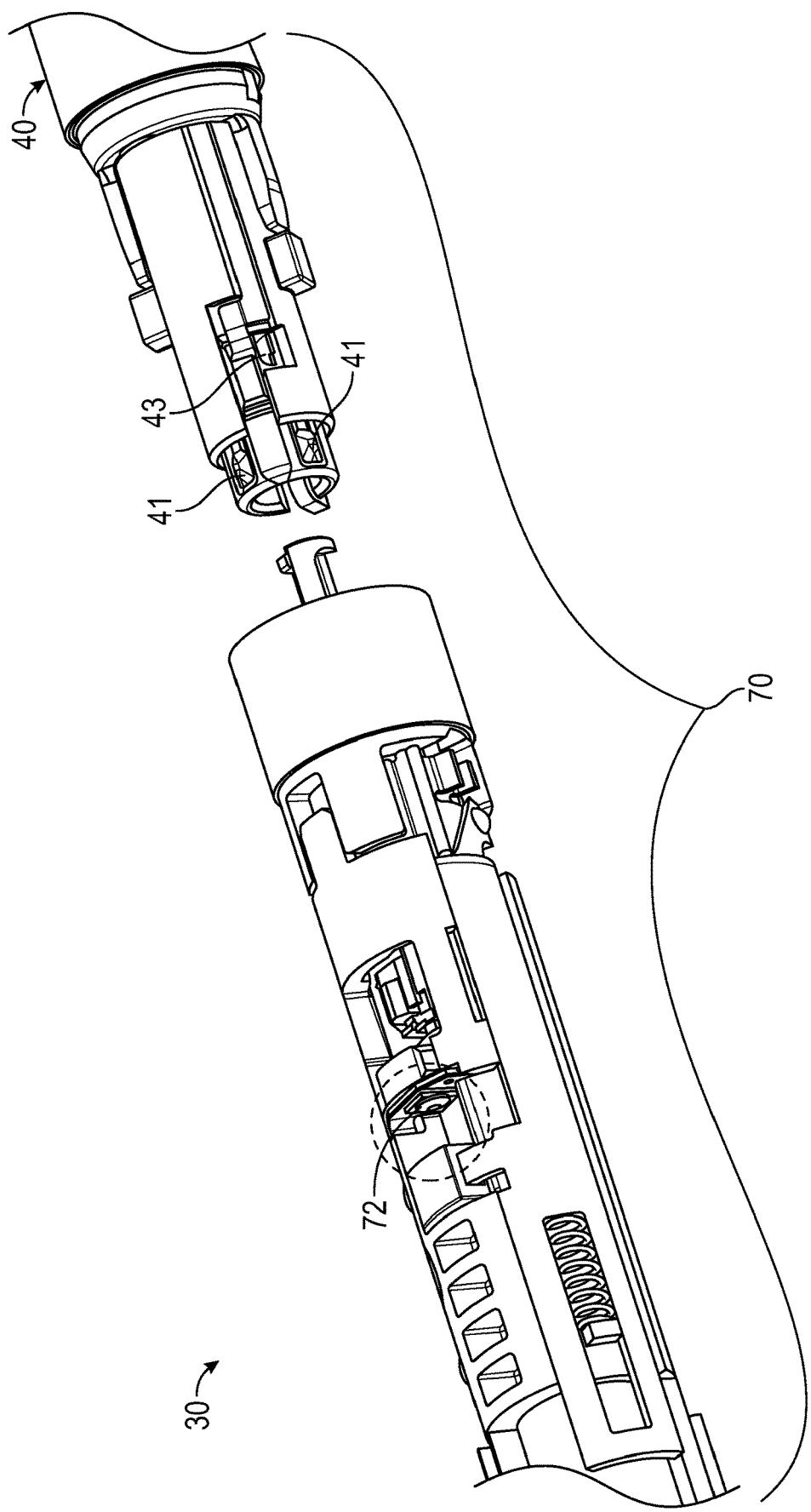
FIG. 7 is a perspective view of the adapter assembly and the loading unit illustrating an activation mechanism according to the present disclosure.

With reference to FIG. 7, the adapter assembly 30 includes an activation mechanism 70, which provides positive feedback to the handle assembly 20 that the loading unit 40 has been properly mounted to the adapter assembly 30, and in conjunction with memory or circuit components disposed within the loading unit 40, provides information to the clinician regarding various parameters of the loading unit 40 (e.g., staple size). The activation mechanism 70 also permits repetitive mounting of multiple loading units 40 without experiencing any degradation of its mechanical and/or electrical components within the adapter assembly 30 thereby enhancing usability and ensuring proper functioning of the adapter assembly 30 over an extended number of uses.

The activation mechanism 70 includes a switch 72, which is actuated in response to insertion of the loading unit 40 into a distal end portion 30c of the adapter assembly 30. The activation mechanism 70 is described in greater detail in a U.S. Patent Application Publication No. 2017/0128067, entitled "Surgical Device," the entire disclosure of which is incorporated by reference herein.

Figure 8:
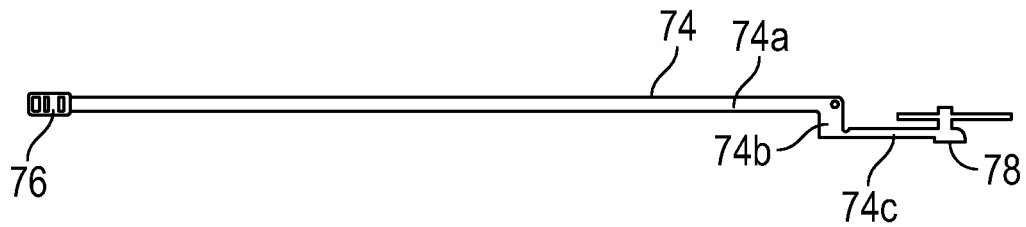
FIG. 8 is a side view of a wiring harness according to an embodiment of the present disclosure.
Figure 9:
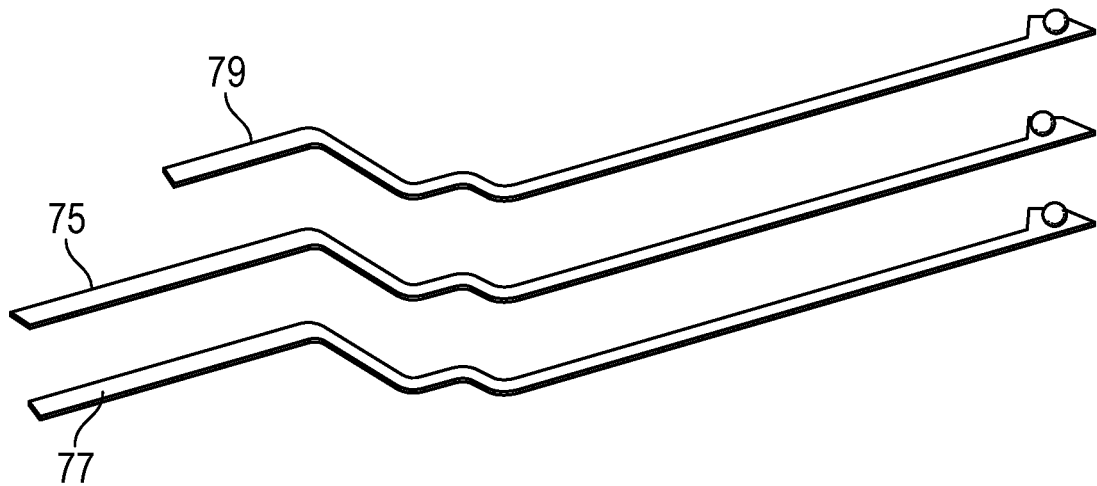
FIG. 9 is a perspective view, with parts separated, of a flexible finger of the wiring harness of FIG. 8 according to an embodiment of the present disclosure.

With reference to FIGS. 8 and 9, a wiring harness 74 connects the switch 72 and electrical contact assemblies 80 and 81 with the electrical connector 32. The wiring harness 74 may be a flexible cable having one or more conductive layer(s) 75 disposed on a first flexible dielectric substrate 77 and a second flexible dielectric substrate 79, which enclose the conductive layer(s) 75. The dielectric substrates 77 and 79 may be formed from any suitable flexible dielectric material including, but not limited to, polyester, polyimide, polyethylene naphthalate, polyetherimide, fluropolymers, polyether ether ketone, and combinations thereof. The conductive layer 75 may include a plurality of traces and may be formed from any conductive material, such as copper, or various alloys, and may be applied to the dielectric substrate using any subtractive (e.g., etching) or additive (e.g., screen printing) technique for forming conductive layers on a flexible dielectric substrate.

Figure 10:
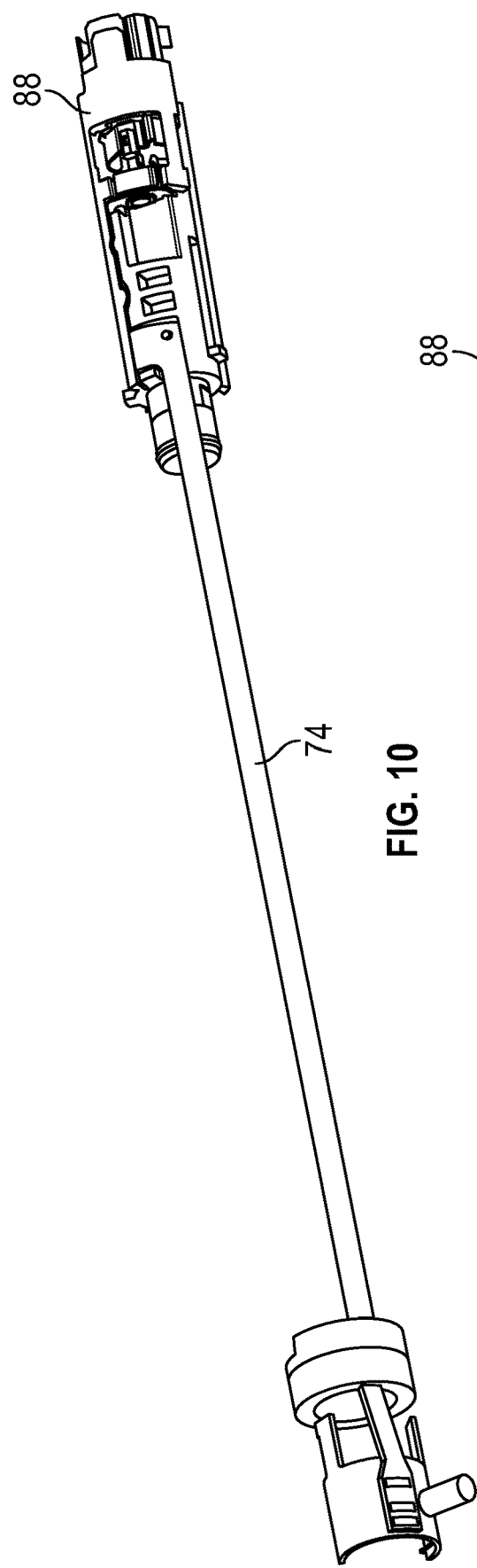
FIG. 10 is a perspective view of internal components of the adapter assembly according to an embodiment of the present disclosure.
Figure 11:
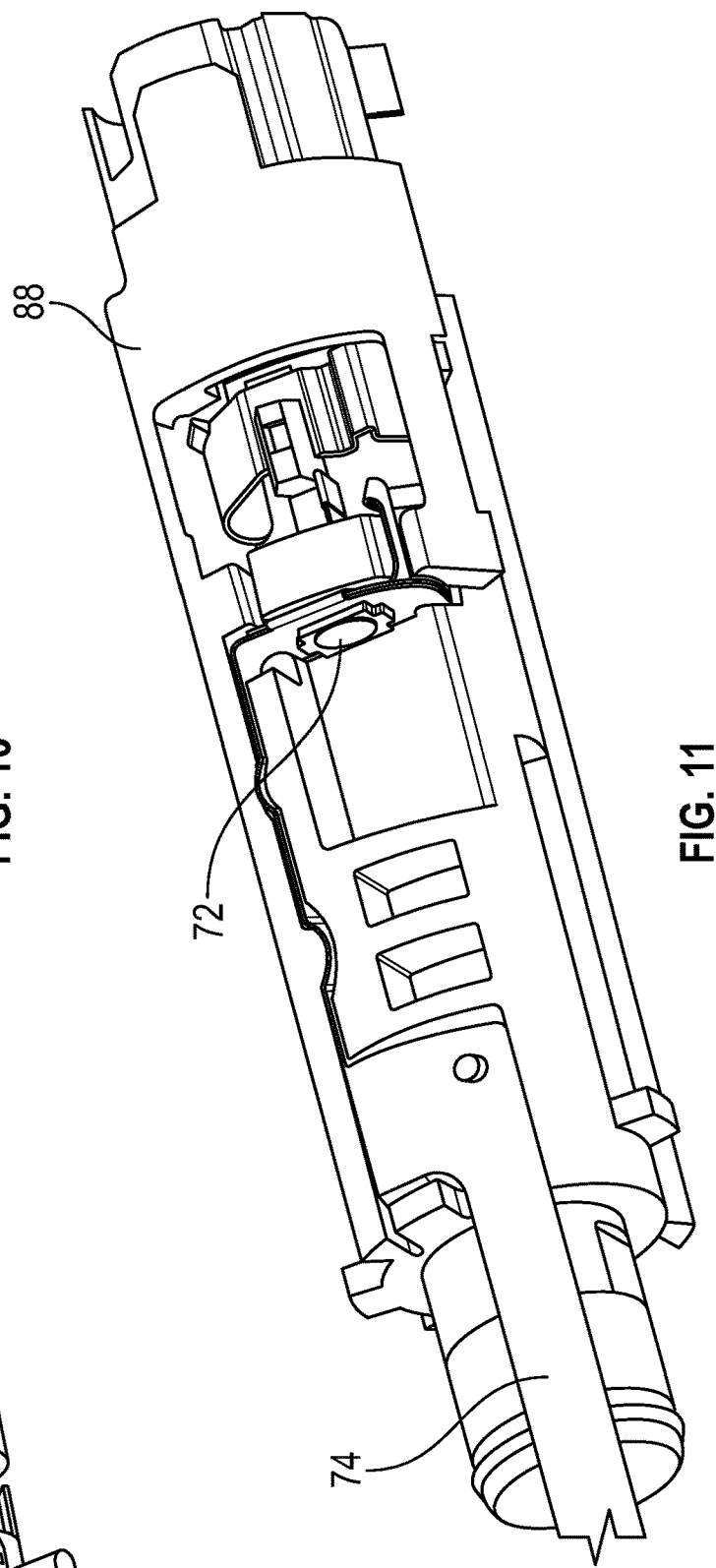
FIG. 11 is a perspective view of a distal end portion of the adapter assembly according to an embodiment of the present disclosure.

The wiring harness 74 may include any number of segments 74a, 74b, 74c to allow for routing through the adapter assembly 30. As shown in FIGS. 10 and 11, the segment 74b is approximately perpendicular with respect to the segments 74b and 74c, allowing for the wiring harness 74 to be wrapped around and within various components of the distal end portion 30c of the adapter assembly 30.

Figure 12:
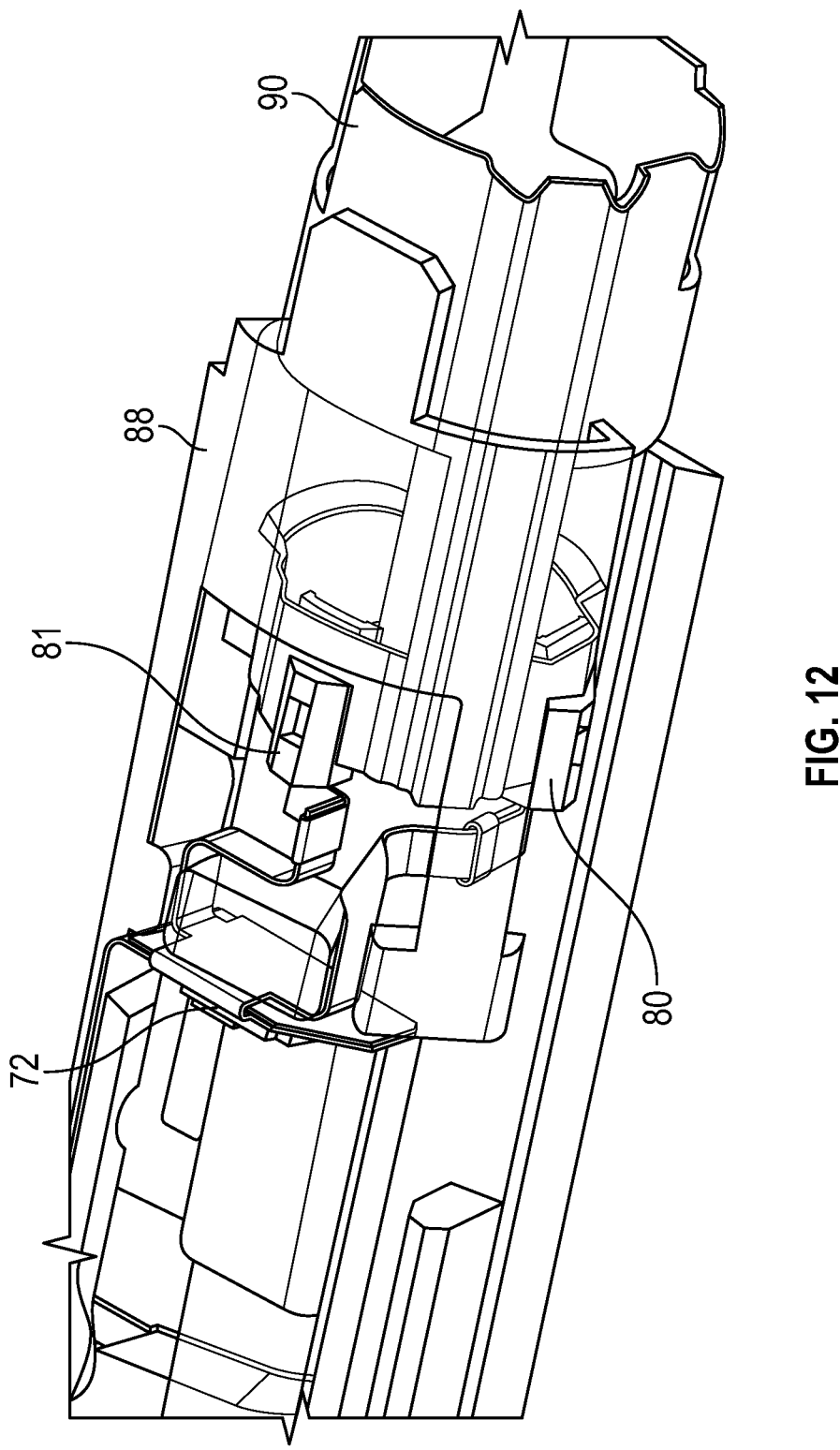
FIG. 12 is a perspective view of the distal end portion of the adapter assembly with flexible fingers coupled to electrical contacts according to an embodiment of the present disclosure.

With reference to FIG. 8, the wiring harness 74 includes a proximal connector portion 76, which is coupled to the electrical connector 32. The wiring harness 74 also includes a distal connector portion 78, which is coupled to the switch 72 and a pair of electrical contact assemblies 80 and 81 (FIGS. 12-14).

With reference to FIG. 7, the loading unit 40 includes a pair of electrical contacts 41, which are configured to engage the pair of electrical contact assemblies 80 and 81 disposed within the distal end portion 30c of the adapter assembly 30 when the loading unit 40 is inserted into the adapter assembly 30. The pair of electrical contacts 41 are coupled to a storage device 43 disposed within the loading unit 40. The storage device 43 may be encrypted and may store information pertaining to the loading unit 40 such as, usage count, sterilization cycles, staple size, jaw size, etc. The storage device 43 may be any suitable non-volatile memory, such as flash memory.

With reference to FIGS. 10-13, the electrical contact assemblies 80 and 81 are disposed at a distal end portion 88 of a rotatable lock member 90, which is configured to rotate about a longitudinal axis defined "X-X" between locked and unlocked positions in response to rotation of the loading unit 40. More specifically, after insertion of the loading unit 40 into the adapter assembly 30, the loading unit 40 is rotated therein to secure the loading unit 40. Accordingly, the rotatable lock member 90 rotates with the loading unit 40 while the electrical contact assemblies 80 and 81 of the rotatable lock member 90 maintain electrical connectivity with the pair of electrical contacts 41 of the loading unit 40.

Figure 13:
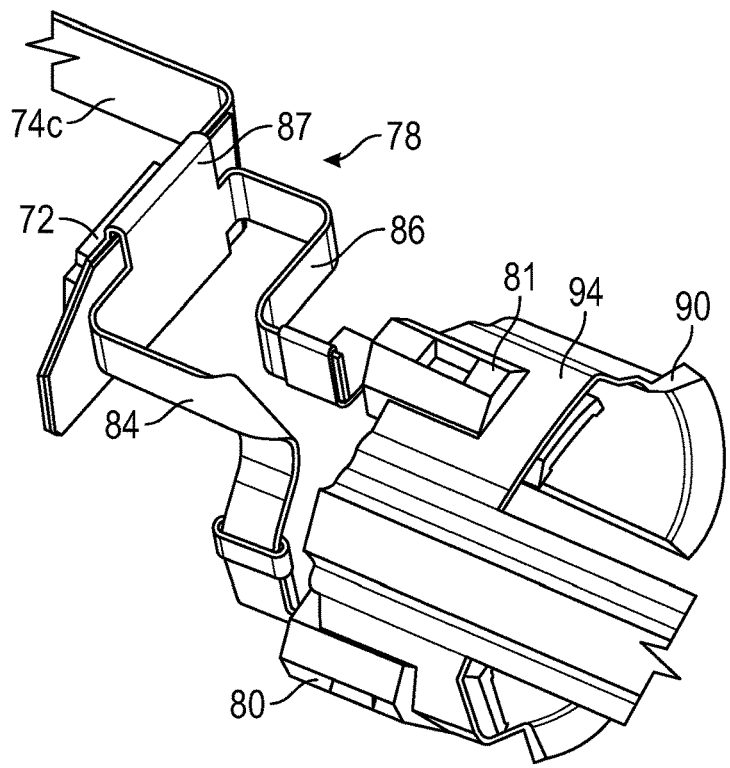
FIG. 13 is a perspective view of the flexible fingers of FIG. 12 coupled to electrical contacts attached to a rotatable lock member according to an embodiment of the present disclosure.
Figure 14:
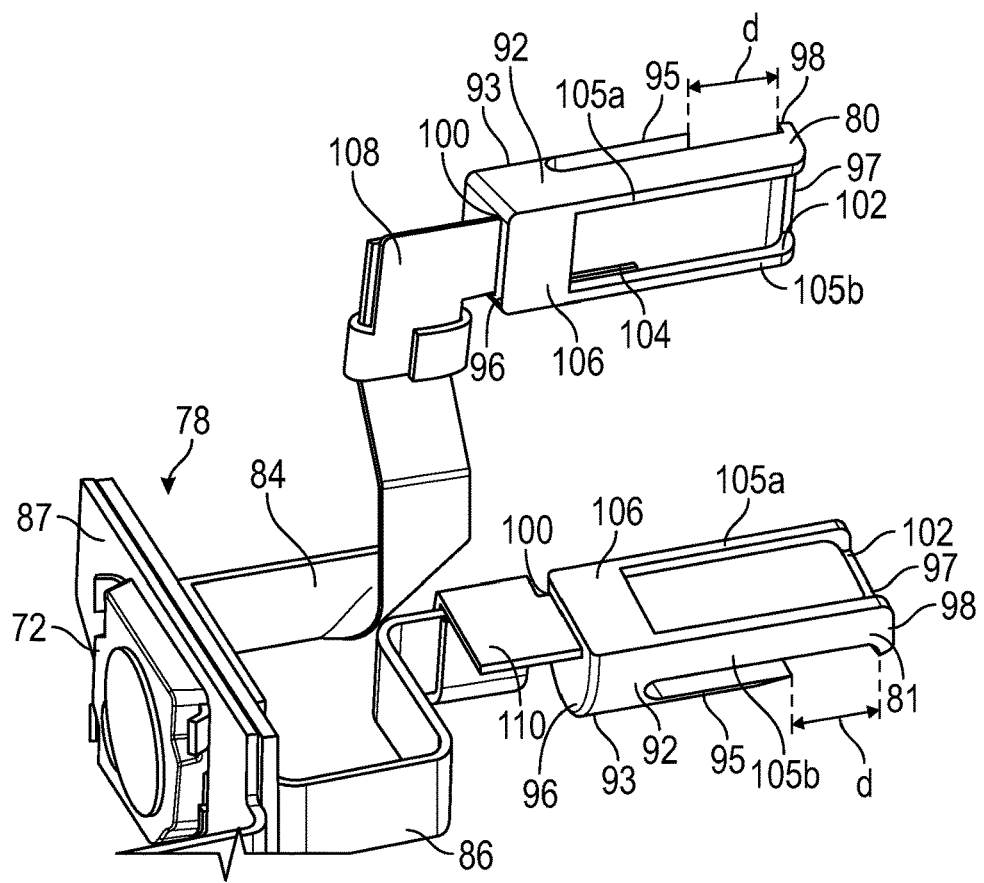
FIG. 14 is a perspective view of the flexible fingers coupled to electrical contacts according to an embodiment of the present disclosure.

As shown in FIGS. 13 and 14, the distal connector portion 78 includes a switch portion 82 coupled to the switch 72, and a pair of fingers 84 and 86 (each of which is coupled to corresponding electrical contact assemblies 80 and 81, respectively). With reference to FIG. 9, only finger 84 is shown for brevity although each of the fingers 84 and 86 is the same or substantially identical. The finger 84 includes a contact portion 85 with a distal portion of the second flexible dielectric substrate 79 being removed to expose the conductive layer 75.

With reference to FIG. 14, each of the electrical contact assemblies 80 and 81 are the same or substantially identical. Accordingly, only the structure and components of the electrical contact assembly 80 are described below for the sake of brevity. The electrical contact assembly 80 includes a clip-on housing 92 configured to clip or snap on to a ring portion 94 (FIG. 13) of the rotatable lock member 90. The clip-on housing 92 may be formed from any suitable high strength tensile material, such as metals and/or thermoplastics. The clip-on housing 92 includes a cantilevered tongue 95 on a first surface 93 thereof and which cantilevered tongue 95 extends from a proximal end portion 96 of the clip-on housing 92. The clip-on housing 92 also includes a lip 98 disposed at a distal end portion 97 thereof, which lip 98 extends toward the first surface 93. The cantilevered tongue 95 is separated from the lip 98 by a predetermine distance "d" which is substantially (e.g., about ±2%) the width of the ring portion 94, such that the clip-on housing 92 can be frictionally secured thereto.

The clip-on housing 92 also includes a slit 100, which transitions into a depression 102 formed on a second surface 104 thereof. The clip-on housing 92 houses a contact clip 108 or 110, each of which is coupled to the contact portion 85 of the fingers 84 and 86. The depression 102 is formed between two opposing walls 105a and 105b and extends from the distal end portion 97 of clip-on housing 92 until reaching a shelf 106. The depression 102 is unobstructed at its distal end allowing for the electrical contacts 41 to slide over an outer surface thereof and in particular the contact clip 108 or 110.

As shown in FIGS. 15 and 16, the contact clip 108 may be formed from a conductive material, such as copper, and may have a planar shape. The contact clip 108 includes a contact portion 112 and an attachment portion 114. The contact portion 112 is configured to slide into the slit 100 and over the depression 102, thereby providing an electrical contact for the electrical contact 41. The contact portion 112 may include one or more protrusions 102a, which secure the contact portion 112 between the walls 105a and 105b. The attachment portion 114 is parallel to the contact portion 112 and is connected thereto by a segment 113 which is perpendicular to the contact portion and the attachment portion 114. Since the contact clip 108 is formed from a metal, the attachment portion 114 may be bent to secure the finger 84 as shown in FIG. 16. In particular, the contact portion 85 of the finger 84 may be electrically coupled to the contact portion 112 of the contact clip 108 via soldering or any other suitable methods. The finger 84 is secured by bending the attachment portion 114 about the finger 84 thereby securing it to the contact clip 108. The finger 84 is placed on the segment 113, namely, parallel thereto, and perpendicular to the contact portion 112. Thereafter, the attachment portion 114 is wrapped once or more about the finger 84, such that the finger 84 is disposed between two layers of the attachment portion 114. The attachment portion 114 may be wrapped about its backside.

Figure 18:
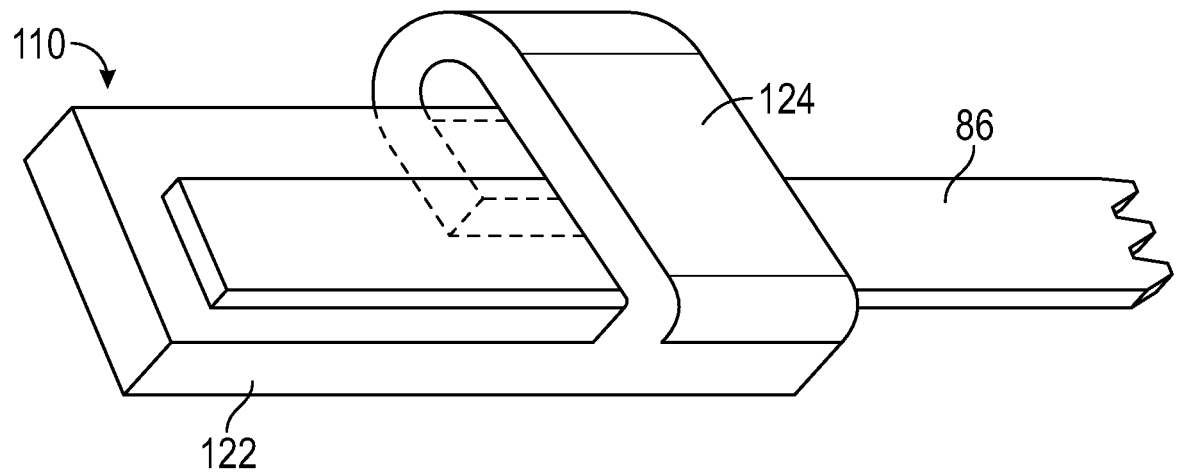
FIG. 18 is a perspective view of the contact clip of FIG. 17.

With reference to FIGS. 17 and 18, the contact clip 110 is substantially similar to the contact clip 108 and only the differences therebetween are described below. The contact clip 110 also includes a contact portion 122, however, an attachment portion 124 is coupled directly to the contact portion 112 and is perpendicular thereto. The finger 86 is placed on the contact portion 122, namely, parallel thereto, and the attachment portion 124 is wrapped once or more about the finger 86, such that the finger 86 is disposed between two layers of the attachment portion 124. The attachment portion 124 may be wrapped about the backside of the contact portion 122. The contact portion 85 of the finger 86 is also electrically coupled to the contact portion 122 of the contact clip 110 via soldering or any other suitable methods.

Figure 19:
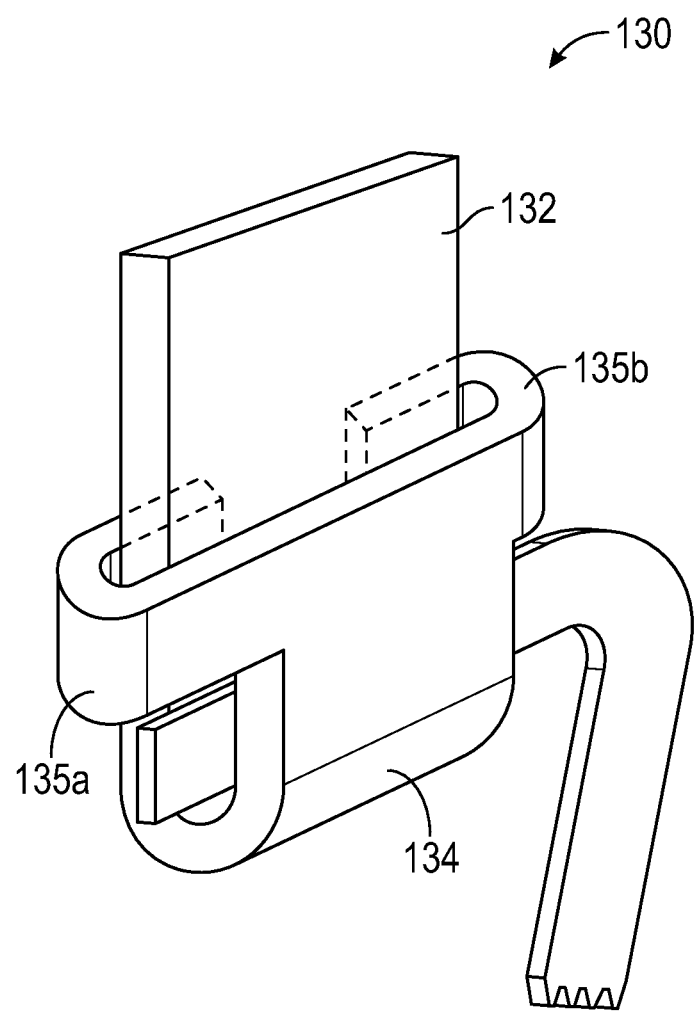
FIG. 19 is a perspective view of a contact clip according to a further embodiment of the present disclosure.

With reference to FIG. 19, a contact clip 130 is substantially similar to the contact clips 108 and 110 and only the differences therebetween are described below. The contact clip 130 includes a contact portion 132 and an attachment portion 134, which extends directly from the contact portion 132 and is parallel thereto. The attachment portion 134 includes a pair of opposing fingers 135a and 135b, which are configured to be wrapped about the contact portion 132. The finger 84 or 86 is placed across the contact portion 132, namely, perpendicular thereto, and the attachment portion 134 is bent onto the contact portion 132. Thereafter, the fingers 135a and 135b are bent about a backside of the contact portion 132.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. A surgical device comprising:
   a handle assembly including a controller;
   a tubular housing having a proximal end portion coupled to the handle assembly, and a distal end portion, the tubular housing including:
   a rotatable lock member disposed at the distal end portion;
   an electrical contact assembly including a clip-on housing configured to attach the electrical contact assembly to the rotatable lock member; and
   a wiring harness disposed within the tubular housing coupled to the electrical contact assembly; and
   a surgical end effector configured to couple to the rotatable lock member, the surgical end effector including an electrical contact configured to couple to the electrical contact assembly.

2. The surgical device according to claim 1, wherein the wiring harness is a flexible cable.

3. The surgical device according to claim 2, wherein the tubular housing further includes a switch actuated in response to the surgical end effector being coupled to the tubular housing.

4. The surgical device according to claim 3, wherein the flexible cable is coupled to the switch and includes a flexible finger coupled to the electrical contact assembly.

5. The surgical device according to claim 4, wherein the electrical contact assembly includes a contact clip secured in a depression formed on the clip-on housing.

6. The surgical device according to claim 5, wherein the flexible finger is electrically coupled to the contact clip.

7. The surgical device according to claim 6, wherein the contact clip includes a contact portion and an attachment portion.

8. The surgical device according to claim 7, wherein the contact portion is configured to engage the electrical contact.

9. The surgical device according to claim 8, wherein the attachment portion is folded over to secure the flexible finger to the contact clip.

10. The surgical device according to claim 9, wherein the flexible finger includes an exposed portion of a conductive layer that is soldered to the contact clip.

11. The surgical device according to claim 1, wherein the clip-on housing includes a cantilevered tongue.

12. The surgical device according to claim 1, wherein the clip-on housing is configured to frictionally engage a ring portion of the rotatable lock member to attach the electrical contact assembly to the rotatable lock member.

13. A surgical device adapter assembly comprising:
- a tubular housing having a proximal end portion configured to couple to a handle assembly, and a distal end portion configured to couple to a surgical end effector;
- a rotatable lock member configured to engage the surgical end effector;
- an electrical contact assembly disposed at the distal end portion, the electrical contact assembly including a clip-on housing configured to attach the electrical contact assembly to the rotatable lock member; and
- a wiring harness disposed within the tubular housing and coupled to the electrical contact assembly.

14. The surgical device adapter assembly according to claim 13, wherein the wiring harness is a flexible cable.

15. The surgical device adapter assembly according to claim 14, wherein the flexible cable includes a flexible finger coupled to the electrical contact assembly.

16. The surgical device adapter assembly according to claim 15, wherein the electrical contact assembly includes a contact clip secured in a depression formed on the clip-on housing and the flexible finger is electrically coupled to the contact clip.

17. The surgical device adapter assembly according to claim 16, wherein the contact clip includes a contact portion and an attachment portion, the contact portion configured to engage an electrical contact of a surgical end effector, and the attachment portion folded over to secure the flexible finger to the contact clip.

18. The surgical device adapter assembly according to claim 17, wherein the flexible finger includes an exposed portion of a conductive layer that is soldered to the contact clip.

19. The surgical device adapter assembly according to claim 13, wherein the clip-on housing includes a cantilevered tongue.

20. The surgical device adapter assembly according to claim 13, wherein the clip-on housing is configured to frictionally engage a ring portion of the rotatable lock member to attach the electrical contact assembly to the rotatable lock member.

* * * * *